United States Patent [19]

Aubert

[11] Patent Number: 5,758,970

[45] Date of Patent: Jun. 2, 1998

[54] DEVICE AND PROCESS FOR THE SIMULTANEOUS MEASUREMENT OF THE EXTENT AND THE TEMPERATURE OF A CRACK AT THE SURFACE OF AN ELECTRICALLY CONDUCTIVE SOLID BODY

[75] Inventor: Jean-Pierre Aubert, Charenton, France

[73] Assignee: Societe Nationale d'Etude et de Construction de Moteurs d'Aviation "Snecma", Paris, France

[21] Appl. No.: 647,886

[22] PCT Filed: Oct. 11, 1995

[86] PCT No.: PCT/FR95/01321

§ 371 Date: Jun. 3, 1996

§ 102(e) Date: Jun. 3, 1996

[30] Foreign Application Priority Data

Oct. 12, 1994 [FR] France ................... 94 12146

[51] Int. Cl.$^6$ ............... G01K 7/08; G01N 27/20
[52] U.S. Cl. ............... 374/142; 374/180; 73/799; 324/718; 324/715
[58] Field of Search ............... 374/142, 180; 73/799; 324/718, 715, 713

[56] References Cited

U.S. PATENT DOCUMENTS

| 2,612,779 | 10/1952 | Mulford | 374/180 |
| 3,258,957 | 7/1966 | Smart | 374/180 |
| 3,756,067 | 9/1973 | Cushman | 374/180 |
| 4,677,855 | 7/1987 | Coffin, Jr. et al. | 73/799 |
| 4,924,708 | 5/1990 | Solomon et al. | 73/799 |
| 5,574,376 | 11/1996 | Topp et al. | 324/529 |

FOREIGN PATENT DOCUMENTS

| 2400706 | 3/1979 | France | 324/718 |
| 0139299 | 12/1979 | German Dem. Rep. | 374/180 |
| 0795035 | 5/1958 | United Kingdom | 374/180 |
| 2125169 | 2/1984 | United Kingdom | 374/180 |

OTHER PUBLICATIONS

Patent Abstracts of Japan, vol. 17, No. 553 (P-1625) 5 Oct. 1993 (JP. 5-157721, 25 Jun. 1993) (only abstract considered).

Patent Abstracts of Japan, vol. 18, No. 78 (P-1689) 8 Feb. 1994 (JP 5-288706, 2 Nov. 1993) (only abstract considered).

*Primary Examiner*—Diego F. F. Gutierrez
*Attorney, Agent, or Firm*—Oblon, Spivak, McClelland, Maier & Neustadt, P.C.

[57] ABSTRACT

Two electrical wires are connected to the surface of an electrically conductive solid body at two measurement points located on either side of a crack in the surface of the body. The two wires form a thermoelectric couple. A constant DC current is applied to the body. The two wires are connected to a device for measuring the extent of the crack and another device for measuring the temperature of the crack. By measuring the potential difference during application and interruption of the DC electric current to the body, it is possible to simultaneously obtain a measurement of the extent of the crack and a measurement of the temperature of the crack.

10 Claims, 2 Drawing Sheets

5,758,970

DEVICE AND PROCESS FOR THE SIMULTANEOUS MEASUREMENT OF THE EXTENT AND THE TEMPERATURE OF A CRACK AT THE SURFACE OF AN ELECTRICALLY CONDUCTIVE SOLID BODY

BACKGROUND OF THE INVENTION

1. Field of the Invention

The invention relates to a device and to a method for the simultaneous measurement of the extent and the temperature of an open crack at the surface of an electrically conductive solid body. It applies especially to the determination of the influence of the temperature conditions on crack propagation, for example when studying the characteristics of the crack resistance of new construction materials for components and assemblies of critical importance in mechanical constructions, as well as components and structures themselves, such as aircraft cell structures or aircraft engine components.

2. Discussion of the Background

Studying the progress of cracks under varied stress conditions, such as temperature variations during mechanical cycling, is a very important problem as it makes it possible to design optimum constructions which ensure a predetermined damage tolerance and a predetermined safety factor.

Various procedures and devices exist for determining the crack parameters in constructions and test specimens. In particular, it is known, from French Patent Application published under No. 2,400,706, to determine the extent of an open crack at the surface of a solid body consisting of an electrically conductive material by studying its electrical resistance; this study is carried out by applying, to this body, an electric current of constant strength in a direction which is preferably as close as possible to the perpendicular to the crack and by measuring the potential difference between two measurement points located on either side of the open crack. In the vicinity of the crack, the current lines are deflected and go around the crack, the increase in path length of these current lines being a function of the extent (depth and/or length) of the crack. The potential difference measured between the two measurement points is therefore representative of the electrical resistance of the body between the two measurement points. The potential difference may be measured by means of two electrical wires placed at two measurement points and connected to a measurement apparatus such as, for example, a crack follower.

In the case of studying crack propagation in an environment subjected to temperature variations, it is also necessary to be able to determine the temperature of the test piece at the crack tip accurately. Temperature measurements may be carried out conventionally by means of a thermocouple pressed against the surface of the test piece. However, this arrangement of the thermocouple does not enable the temperature to be measured at the very place of the crack and does not enable sufficient measurement reproducibility and reliability to be achieved.

SUMMARY OF THE INVENTION

The object of the invention is to solve this problem and to produce a method and a device for the simultaneous measurement of the extent and the temperature of an open crack at the surface of an electrically conductive solid body at the very place of this crack and without using an external thermocouple. To do this, the invention consists in connecting, at two measurement points located on either side of the crack, two electrical wires forming a thermoelectric couple, in periodically applying a DC electric current of constant strength in the body in a direction preferably perpendicular to the crack, in measuring the potential difference between these two measurement points respectively during two successive phases of application and of interruption of the electric current, in processing the potential difference values measured in order simultaneously to deduce therefrom the extent of the crack and the temperature at the crack tip.

According to the invention, the device for the simultaneous measurement of the extent and the temperature of a crack at the surface of an electrically conductive solid body, a DC electric current of constant strength passing periodically through this body in a direction which is as close as possible to the perpendicular to the crack, is characterized in that it includes two electrical wires forming a thermoelectric couple, these two wires being connected at two measurement points located on either side of the crack and connected up, on the one hand, to two input terminals of a device for measuring the extent of the crack and, on the other hand, to two input terminals of a device for measuring the temperature at the crack.

The invention also relates to a method for the simultaneous measurement of the extent and the temperature of a crack at the surface of an electrically conductive solid body, this method consisting in periodically passing a DC electric current of constant strength through the body in a direction which is as close as possible to the perpendicular to the crack, characterized in that it consists:

- in connecting, at two measurement points located on either side of the crack, two electrical wires forming a thermoelectric couple,
- in measuring, by means of the two electrical wires, the potential difference between the two measurement points during a phase of interruption of the DC electric current, this potential difference being representative of the temperature of the body at the crack,
- in measuring, by means of the two electrical wires, the potential difference between the two measurement points during a phase of application of the DC electric current, this potential difference including a component representative of the extent of the crack and a component representative of the temperature of the body at the crack,
- in processing the potential difference values measured in order simultaneously to deduce therefrom the extent of the crack and the temperature of the body at the crack.

BRIEF DESCRIPTION OF THE DRAWINGS

Other features and advantages of the invention will appear clearly in the rest of the description given by way of non-limiting example and with regard to the appended figures which represent.

DESCRIPTION OF THE PREFERRED EMBODIMENTS

Figure 1:
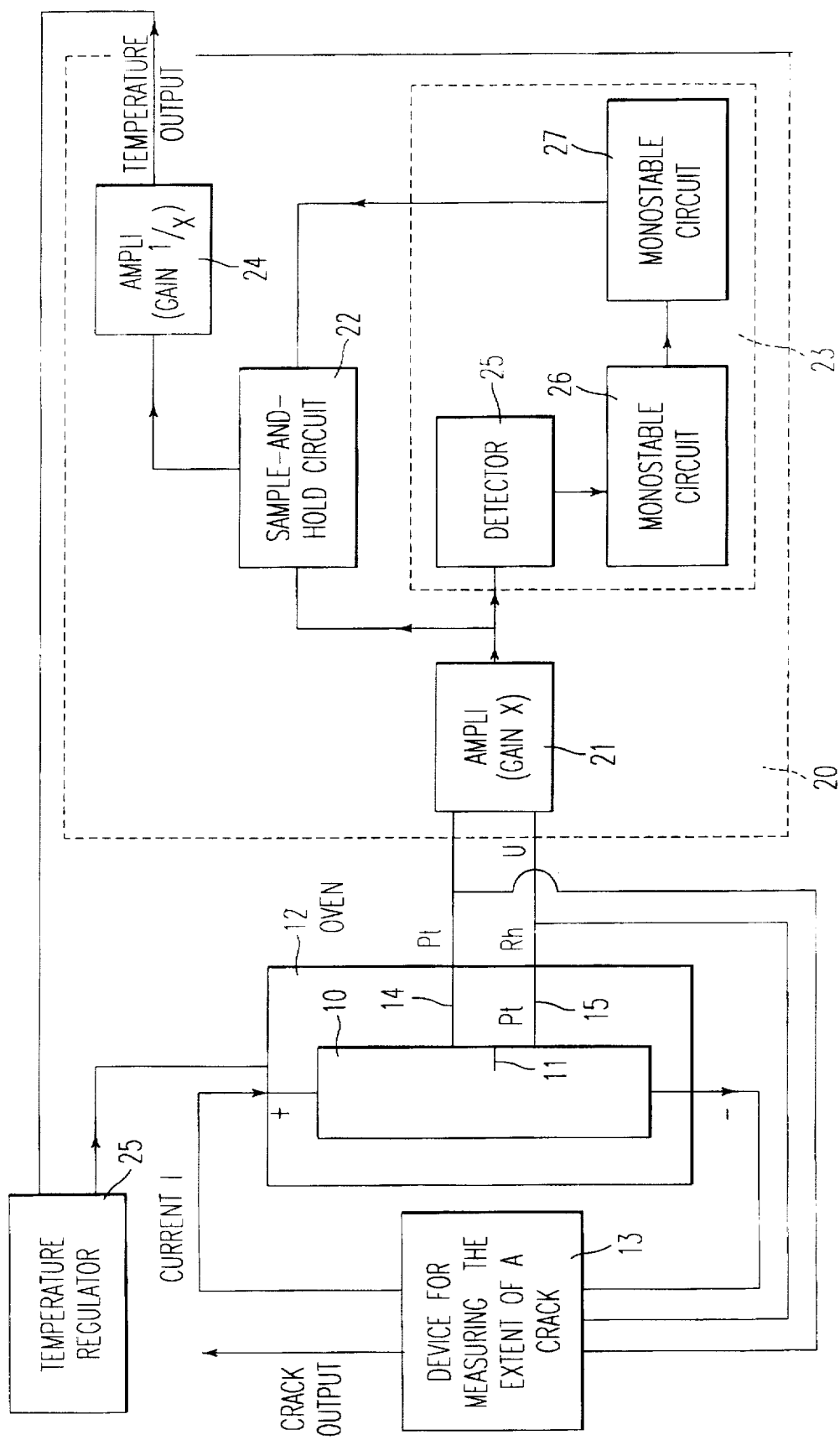
FIG. 1, a block diagram of the device for the simultaneous measurement of the extent and temperature of a crack, according to the invention.

FIG. 1 represents a block diagram of the device for the simultaneous measurement of the extent and the temperature of an open crack at the surface of an electrically conductive solid body, according to the invention.

A solid body 10 having a crack 11 is arranged inside an oven 12.

Figure 2:
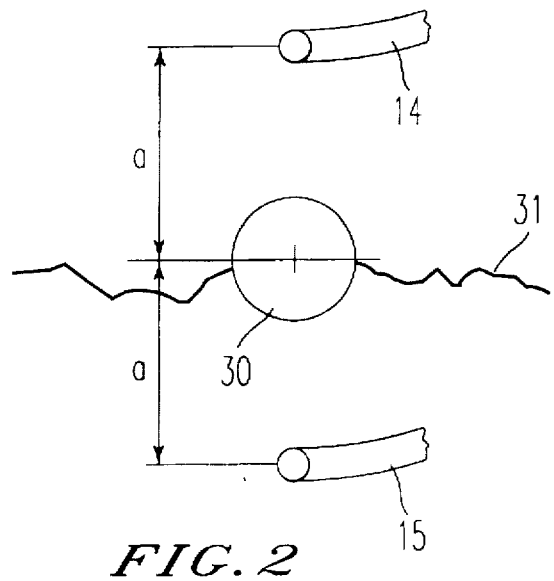
FIG. 2, an example of the arrangement of the electrical wires enabling the simultaneous measurements of the extent of the crack and the temperature at the crack to be carried out.

A DC electric current I of constant strength, delivered by a device for measuring the extent of a crack, such as, for example, a crack follower 13, is periodically applied to the solid body 10 in a direction approximately perpendicular to the crack 11. Two electrical wires 14, 15 forming a thermoelectric couple are connected at two measurement points located on either side of the crack 11. FIG. 2 shows an example of the arrangement of the two electrical wires 14, 15. In this example, the two electrical wires 14, 15 are soldered on either side of and at an equal distance "a" from a crack-initiator 31 and defect 30, this defect 30 being a hole drilled by electrical discharge machining and passing through the wall of the solid body. The two wires 14, 15 consist, for example, respectively of platinum and platinum-10% rhodium.

The two electrical wires 14, 15 are respectively connected up to two inputs of the crack follower 13 which is intended to deliver as output an electrical signal representative of the extent of the crack. The two electrical wires 14, 15 are also connected up to two inputs of a device 20 for measuring the temperature at the crack tip.

The output of the device 20 for measuring the temperature of the crack is connected up to an input of a temperature regulator 25 of the oven 12.

The device 20 for measuring the temperature includes a high input-impedance amplifier 21 of gain X having an output connected, on the one hand, to one input of a sample-and-hold circuit 22 which is intended to measure the potential difference U between the two measurement points and, on the other hand, to means 23 for controlling the sample-and-hold circuit 22. The output of the sample-and-hold circuit 22 is connected to an input of an amplifier 24 of gain 1/X which is intended to deliver as output an electrical signal representative of the temperature at the crack tip in line with the two measurement points.

The operation of the device represented in FIG. 1 is as follows.

When the DC current I passes through the solid body 10, the potential difference U between the two measurement points includes a component representative of the electrical resistance of the body 10 between these two measurement points and a component representative of the thermoelectric effect between these two measurement points. When no DC current I passes through the solid body 10, the potential difference U between the two measurement points is solely due to the thermoelectric effect. The measurements of the extent and the temperature of the crack are then carried out simultaneously in the manner described hereinbelow.

In order to obtain a measurement of the extent of the crack, the crack follower 13 measures the potential difference between the two measurement points at two different instants chosen respectively during two successive phases of application and of interruption of the DC current I and takes the difference between these two measurements. The electrical signal thus obtained is representative of the extent of the crack.

In order to obtain a measurement of the temperature at the crack tip, the device 20 for measuring the temperature measures the potential difference between the two measurement points at an instant chosen during a phase of interruption of the DC current I. For this purpose, the means 23 for controlling the sample-and-hold circuit 22 include, in series, a detector 25 intended to detect the start of the phase of interruption of the DC current I; a first monostable circuit 26 intended to delay the triggering of the measurement of the potential difference between the two measurement points for a predetermined time, for example for 2.5 ms, so as to prevent this measurement from being carried out too soon, during the transitory phase of cancellation of the current I in the body 10; a second monostable circuit 27 controlled by the first monostable circuit 26 and intended to trigger and stop the sample-and-hold circuit 22. The measurement of the potential difference U between the two measurement points is taken over a time imposed by the second monostable circuit 27. This time is chosen to be equal to the period of the principal parasitic signal to which the measurement device is sensitive, so as to eliminate the influence of this parasitic signal.

In general, the principal interference is due to the alternating electromagnetic field radiated by the mains, with a frequency of 50 Hz in Europe. In this case, the time over which the measurement is taken is chosen to be equal to 1/50th of a second. After amplification in the amplifier 24, the electrical signal obtained as output of the sample-and-hold circuit, representative of the temperature at the crack tip at the instant of measurement, is used by the temperature regulator 25 for regulating the temperature of the oven 12.

As the thermoelectric effect may be greater than the electric effect and as the crack follower has a limited input voltage, the two electrical wires 14, 15 forming a thermoelectric couple are preferably soldered at the two measurement points in a connection direction so that the potential difference representative of the thermoelectric effect is in opposition with respect to the potential difference representative of the electric effect induced by passing the DC current I through the solid body 10. Thus, during the phase of application of the DC current I, the potential difference U between the two measurement points is then representative of the difference between the component due to the electric effect and the component due to the thermoelectric effect, and has an order of magnitude compatible with the crack follower.

Figure 3A:
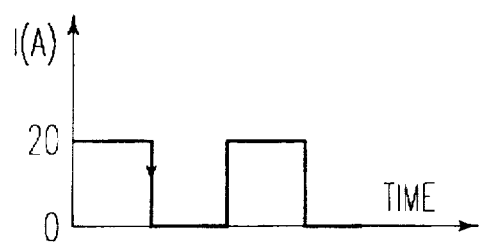
FIGS. 3a and 3b, two examples of chronograms relating respectively to an example of an electric current applied to a solid body perpendicularly to the crack and to a corresponding example of the potential difference between two points located on either side of the crack.
Figure 3B:
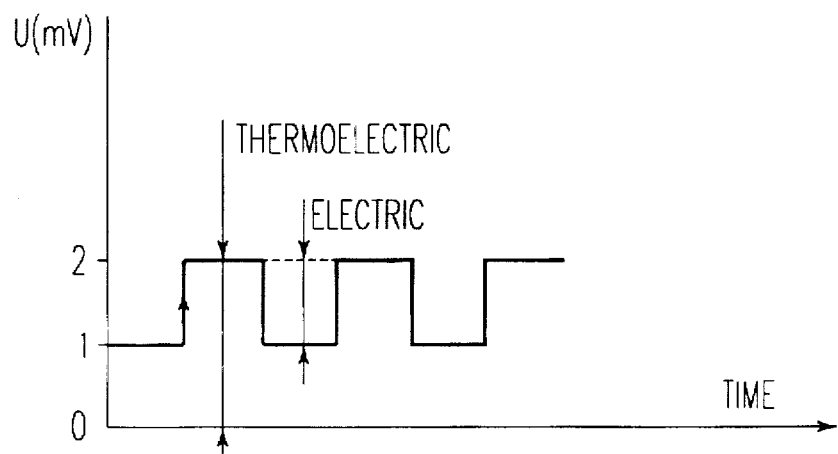

FIGS. 3a and 3b represent two examples of chronograms relating respectively to an example of a DC electric current I applied to the solid body 10 and to an example of the corresponding potential difference U. The chronogram 3b corresponds to the case where the two electrical wires 14, 15 are soldered in a connection direction so that the potential differences representative of the electric effect and of the thermoelectric effect are in opposition and to the case where the thermoelectric effect is greater than the electric effect.

FIG. 3b shows that in these conditions the value of the potential difference U between the two measurement points is lower during the phase of application of the DC current I to the solid body 10 than during the phase of interruption of this current I. The start of the phase of interruption of the DC current I may then be determined by the detector 25 by detecting the rising edge of the potential difference U.

The invention is not limited to the embodiment specifically described; in particular, the electrical wires 14, 15 may consist of materials other than platinum and platinum-10% rhodium insofar as these materials constitute a thermoelectric couple.

I claim:

1. Device for the simultaneous measurement of an extent of a crack and a temperature of said crack at a surface of an electrically conductive solid body, comprising:

means for applying a constant DC electric current through said solid body in a direction close to perpendicular to said crack;

means for interrupting said DC electric current;

two electrical wires forming a thermoelectric couple;

said two wires being connected to said solid body at two measurement points located on opposite sides of said crack; and said two wires being connected to two input terminals of a measuring means in order to measure the extent of the crack during a phase of application of the DC electric current and also being connected to two other input terminals of the measuring means in order to measure the temperature at the crack during a phase of interruption of the DC electric current.

2. Device according to claim 1, wherein the device for measuring the temperature includes a sample-and-hold circuit for measuring the potential difference between the two measurement points during the phase of interruption of the DC current through the body and means for controlling the sample-and-hold circuit.

3. Device according to claim 2, wherein the means for controlling includes, in series, a detector for detecting the start of the phase of interruption of the DC current, a first monostable circuit for delaying the triggering of the measurement of the potential difference for a predetermined time, and a second monostable circuit controlled by the first monostable circuit for triggering and stopping a sample-and-hold circuit.

4. Device according to claim 3, characterized in that said two electrical wires consist respectively of platinum and platinum-10% rhodium.

5. Device according to claim 4, wherein the two wires are soldered at the two measurement points so that the potential difference representative of a thermoelectric effect induced by the temperature is in opposition with respect to an electric effect induced by passing the DC current through the body.

6. Device according to claim 3, wherein the two wires are soldered at the two measurement points so that the potential difference representative of a thermoelectric effect induced by the temperature is in opposition with respect to an electric effect induced by passing the DC current through the body.

7. Device according to claim 2, wherein the two wires are soldered at the two measurement points so that the potential difference representative of a thermoelectric effect induced by the temperature is in opposition with respect to an electric effect induced by passing the DC current through the body.

8. Device according to claim 1, wherein the two wires are soldered at the two measurement points so that the potential difference representative of a thermoelectric effect induced by the temperature is in opposition with respect to an electric effect induced by passing the DC current through the body.

9. Method for the simultaneous measurement of an extent of a crack and the temperature of said crack at a surface of an electrically conductive solid body, comprising the steps of:

periodically passing a constant DC electric current through said solid body in a direction close to perpendicular to said crack;

connecting two electrical wires to said solid body at two measurement points located on opposite sides of said crack to form a thermoelectric couple;

measuring, by means of said two electrical wires, a first potential difference between the two measurement points during a phase of interruption of the DC electric current, to detect the temperature of said body at the crack;

measuring, by means of said two electrical wires, a second potential difference between the two measurement points during a phase of application of the DC electric current, the second potential difference including a first component indicating the extent of said crack and a second component indicating the temperature of said body at said crack; and processing the measured first potential difference and the measured second potential difference to determine the temperature of said body at said crack and the extent of said crack, respectively.

10. Method according to claim 9, wherein the measurement of the first potential difference during the phase of interruption of the DC current is taken over a time chosen to be equal to the period of a parasitic signal.

* * * * *